US008881998B1

(12) United States Patent
Sinkfield et al.

(10) Patent No.: US 8,881,998 B1
(45) Date of Patent: Nov. 11, 2014

(54) PORTABLE MISTING TRAILER SYSTEM FOR PREVENTING BODIES FROM OVERHEATING AND REGULATING BODY TEMPERATURE

(76) Inventors: Joseph Sinkfield, Miami, FL (US); C. Brian Hart, Opa Locka, FL (US)

(*) Notice: Subject to any disclaimer, the term of this patent is extended or adjusted under 35 U.S.C. 154(b) by 419 days.

(21) Appl. No.: 13/308,863

(22) Filed: Dec. 1, 2011

(51) Int. Cl.
*A01G 25/09* (2006.01)

(52) U.S. Cl.
USPC ........... 239/172; 239/128; 239/273; 239/279; 239/280.5; 239/281; 239/289; 239/373; 239/536; 239/550; 239/565; 134/123; 62/259.4; 119/665; 4/616

(58) Field of Classification Search
CPC .... B05B 9/007; B05B 15/061; B05B 15/062; B05B 15/00; B05B 9/0805; B05B 1/262; B05B 15/069; A01M 7/0082; A01G 25/00; B60S 3/04; A47L 15/23; F24F 5/0035; A01K 13/00; A47C 3/286
USPC ......... 239/128, 146, 172, 273, 276, 279, 280, 239/280.5, 289, 373, 536, 543, 548, 550, 239/565, 566, 567, 722, 281; 134/45, 123, 134/174; 62/259.4; 119/665, 667, 671; 4/616
See application file for complete search history.

(56) References Cited

U.S. PATENT DOCUMENTS

| | | | | |
|---|---|---|---|---|
| 2,221,876 A | * | 11/1940 | Mackin | 239/549 |
| 2,751,882 A | * | 6/1956 | Coyner | 134/123 |
| 3,072,131 A | * | 1/1963 | Di Laurenzio | 239/722 |
| 3,584,446 A | * | 6/1971 | Bernshausen | 239/172 |
| 3,949,709 A | * | 4/1976 | Myers | 119/667 |
| 4,643,354 A | * | 2/1987 | Stowe | 239/172 |
| 4,972,803 A | * | 11/1990 | Stump | 119/671 |
| 5,337,960 A | * | 8/1994 | Allen | 239/280.5 |
| 5,598,719 A | | 2/1997 | Jones et al. | |
| 6,000,631 A | * | 12/1999 | Lamminen et al. | 239/273 |
| 6,161,362 A | | 12/2000 | Forbis, Sr. et al. | |
| D488,208 S | | 4/2004 | Cook | |
| 7,137,269 B1 | | 11/2006 | Maranville | |
| 7,334,744 B1 | | 2/2008 | Dawson | |
| 7,395,616 B2 | | 7/2008 | Fallon | |

OTHER PUBLICATIONS www.amazon.com; Port-A-Cool Portable Evaporative Cooling Unit; Internet; as of Feb. 25, 2011.
www.rapidcool.com; Evaporative Cooling System; Internet; as of Feb. 25, 2011.
www.amazon.com; Orbit Portable ¼ Inch Outdoor Mist Cooling System; Internet; as of Feb. 25, 2011.

* cited by examiner

Primary Examiner — Steven J Ganey

(57) ABSTRACT

A portable misting trailer system for preventing bodies from overheating and regulating body temperature, having a trailer frame with a first and second side bar secured to a portable trailer base, a plurality of arched tubes having a first and second end, the first end of each tube attaches to the first side bar, the second end of each tube attaches to the second side bar, a plurality of misting heads on the arched tubes fluidly connected thereto, a water system within the trailer frame having a storage tank fluidly connected to a water pump that is operatively connected to a power source which is operatively connected to an on-off switch, whereupon turning on the on-off switch activates the pump to pump water from the water tank into the plurality of the arched tubes, whereupon water would exit the arched tubes via the misting heads.

2 Claims, 10 Drawing Sheets

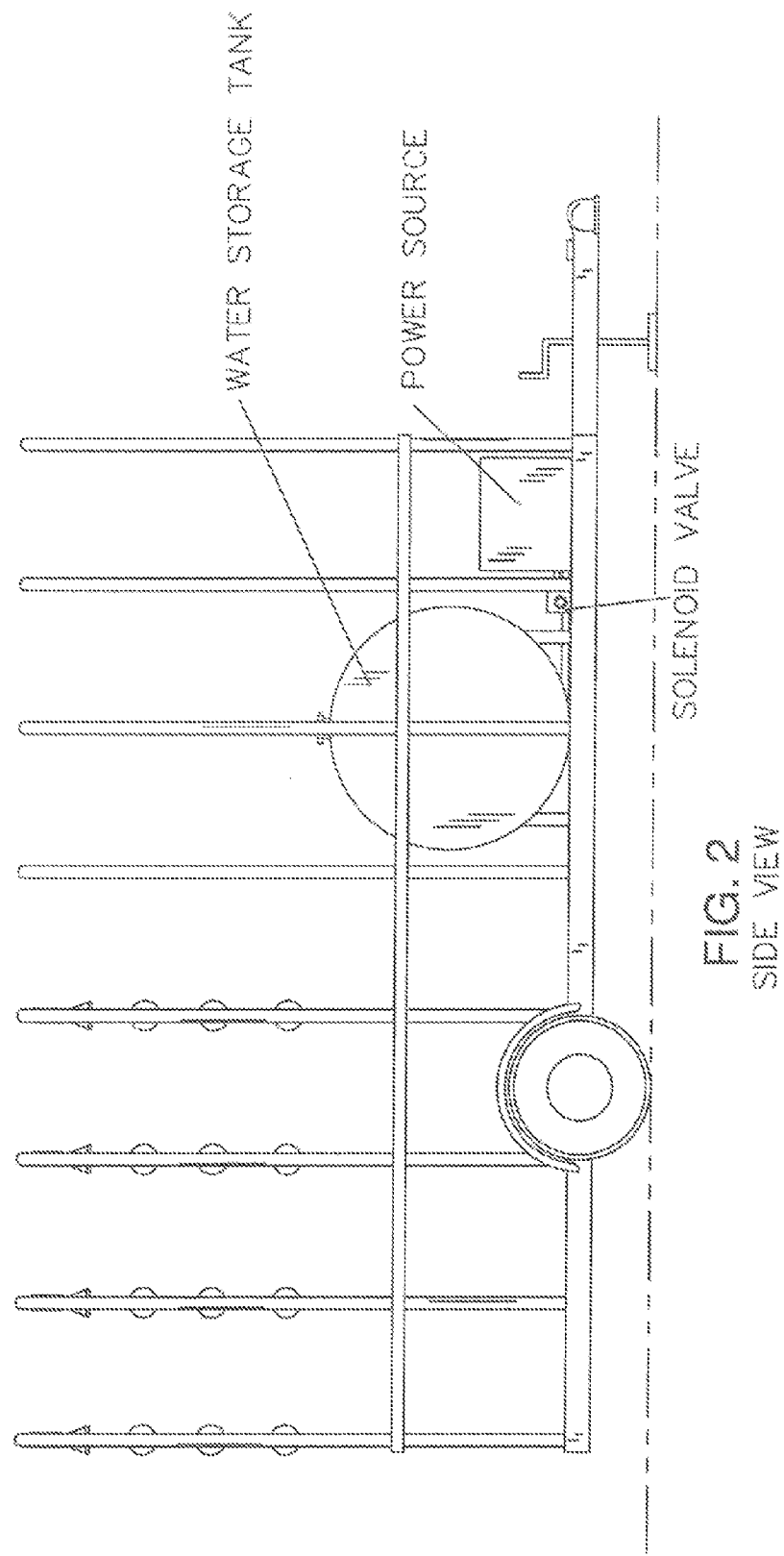

FRONT VIEW

TOP VIEW

PORTABLE MISTING TRAILER SYSTEM FOR PREVENTING BODIES FROM OVERHEATING AND REGULATING BODY TEMPERATURE

BACKGROUND OF THE INVENTION

The present invention is directed to a portable misting trailer system for preventing bodies from overheating and regulating body temperature.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 2 shows a side view of the portable misting trailer system.

DESCRIPTION OF PREFERRED EMBODIMENTS

Figure 1A:
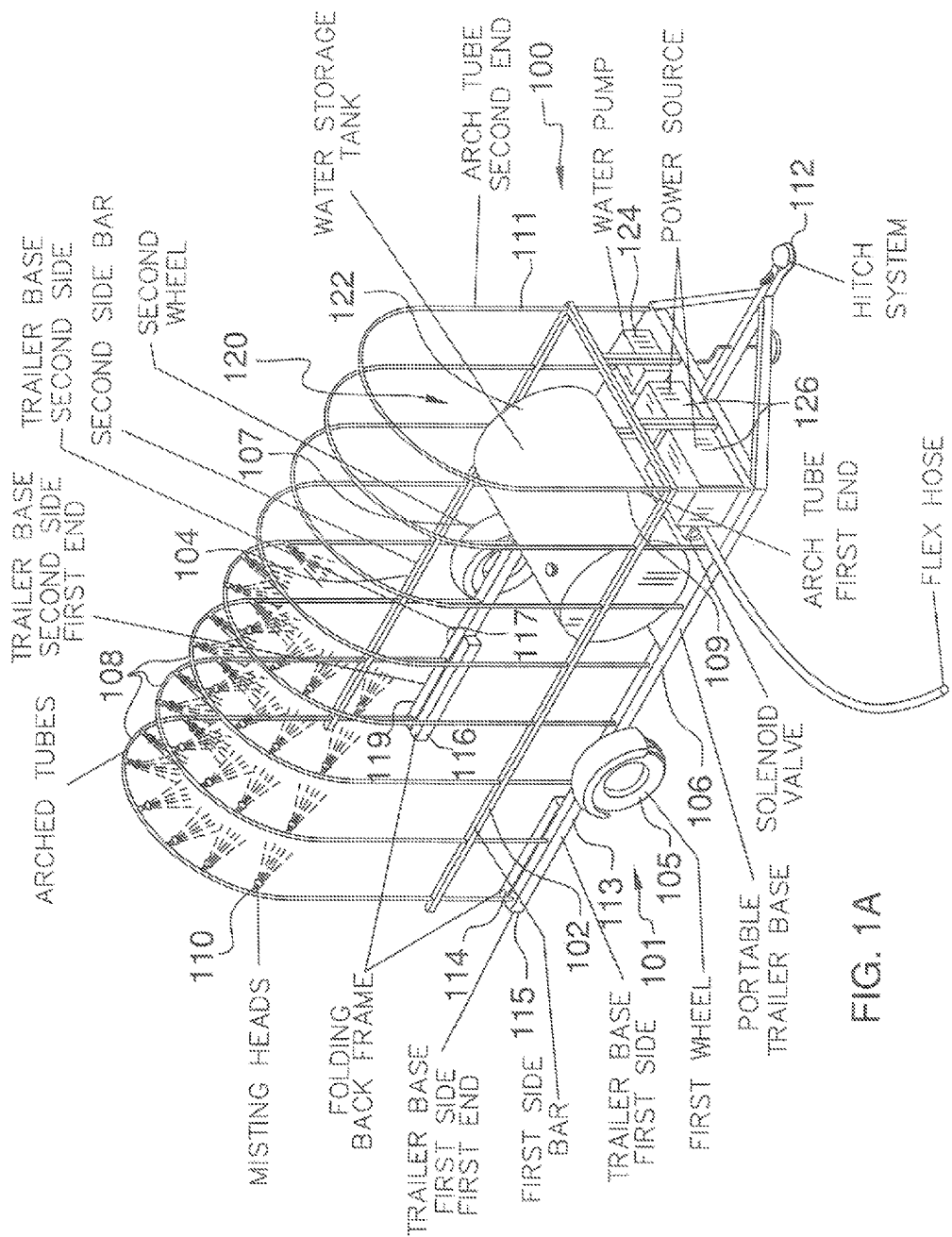
FIG. 1A shows a portable misting trailer system.

Referring now to FIG. 1A, the present invention features a portable misting trailer system (100) for preventing bodies from overheating and regulating body temperature. In some embodiments the system comprises a trailer frame (101) having a first side bar (102) and a second side bar (104), wherein the first and second side bars are secured to a portable trailer base (106); a plurality of arched tubes (108) having an arched-tube first end (109) and an arched-tube second end (111), the first end (109) of each tube attaching to the first side bar (102), the second end (111) of each tube attaching to the second side bar (104); a plurality of misting heads (110) disposed on the arched tubes and fluidly connected thereto; a water system (120) disposed within the trailer frame (101), the water system comprises a storage tank (122), which is fluidly connected to a water pump (124), that is operatively connected to a power source (126), the power source being operatively connected to an on-off switch;

In some embodiments the arched tubes (108) are hollow or have interior channels that fluidly connect them to the water tank (122), whereupon turning on the on-off switch activates the pump (124) to pump water from the water tank (122) into the plurality of the arched tubes (108), whereupon water would exit the arched tubes via the misting heads (110).

In some embodiments the trailer base (106) further comprises a first wheel (105) attached to the trailer-base-first side (113) and a second wheel (107) attached to the trailer-base-second-side (117). In some embodiments the trailer base (106) further comprises a hitch system (112) disposed at the trailer base (106) front end;

In some embodiments the trailer-base-first-side (113) has a trailer-base-first-side first end (115), and the trailer-base-second-side (117) has a trailer-base-second-side first end (119), and further comprises a first-folding-back-frame (114) pivotably attached to the trailer-base-first-side first end (115) and a second-folding-back-frame (116) pivotably attached to the trailer-base-second-side first end (119).

Figure 1B:
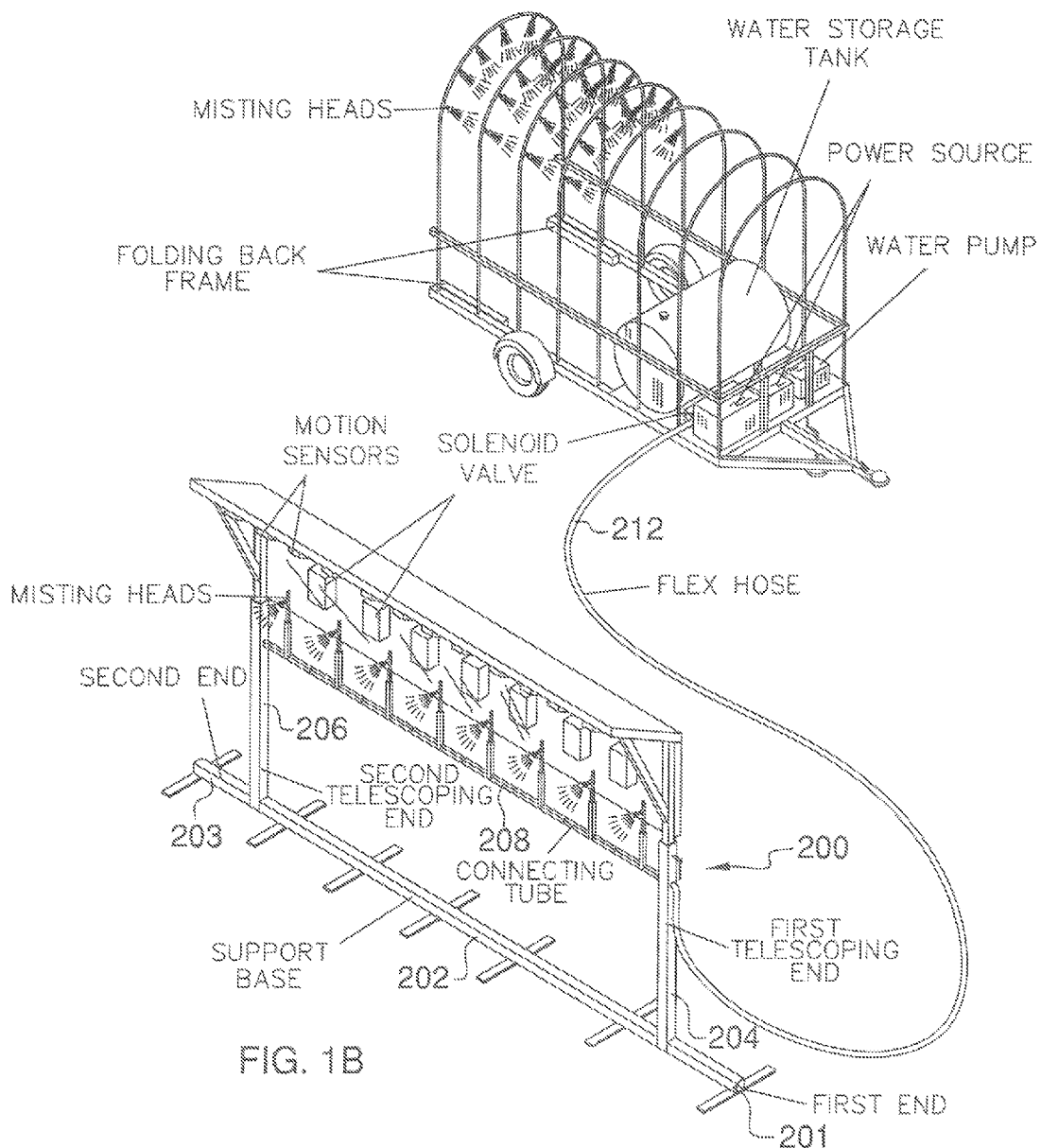
FIG. 1B shows an auxiliary misting station.
Figure 3:
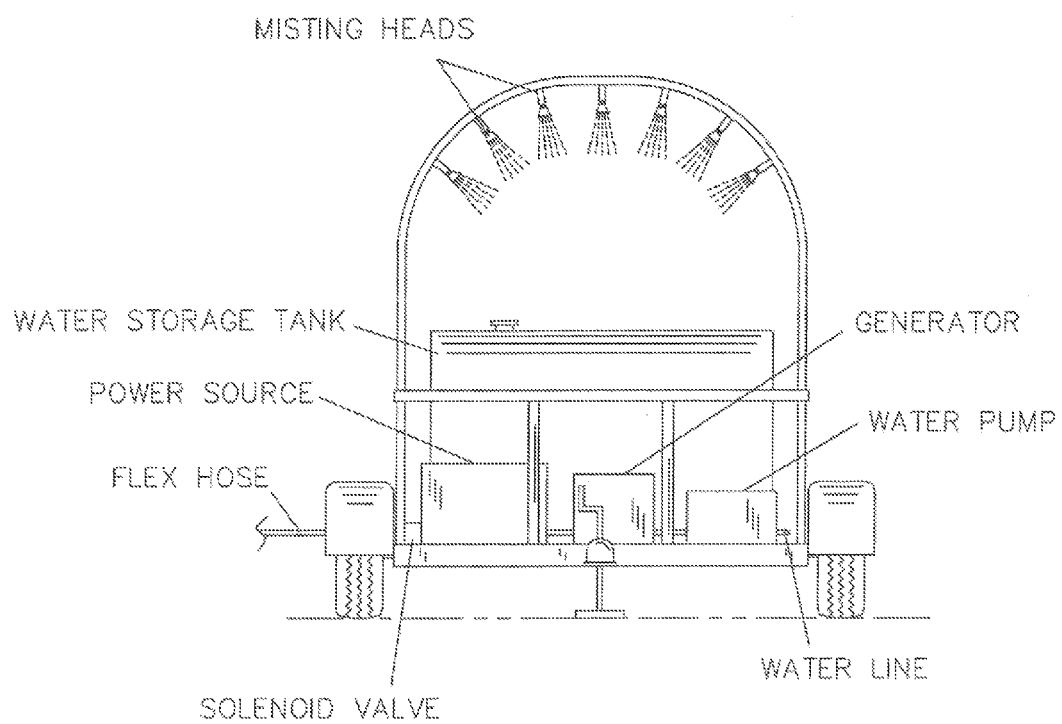
FIG. 3 shows a front view of the portable misting trailer system.
Figure 4:
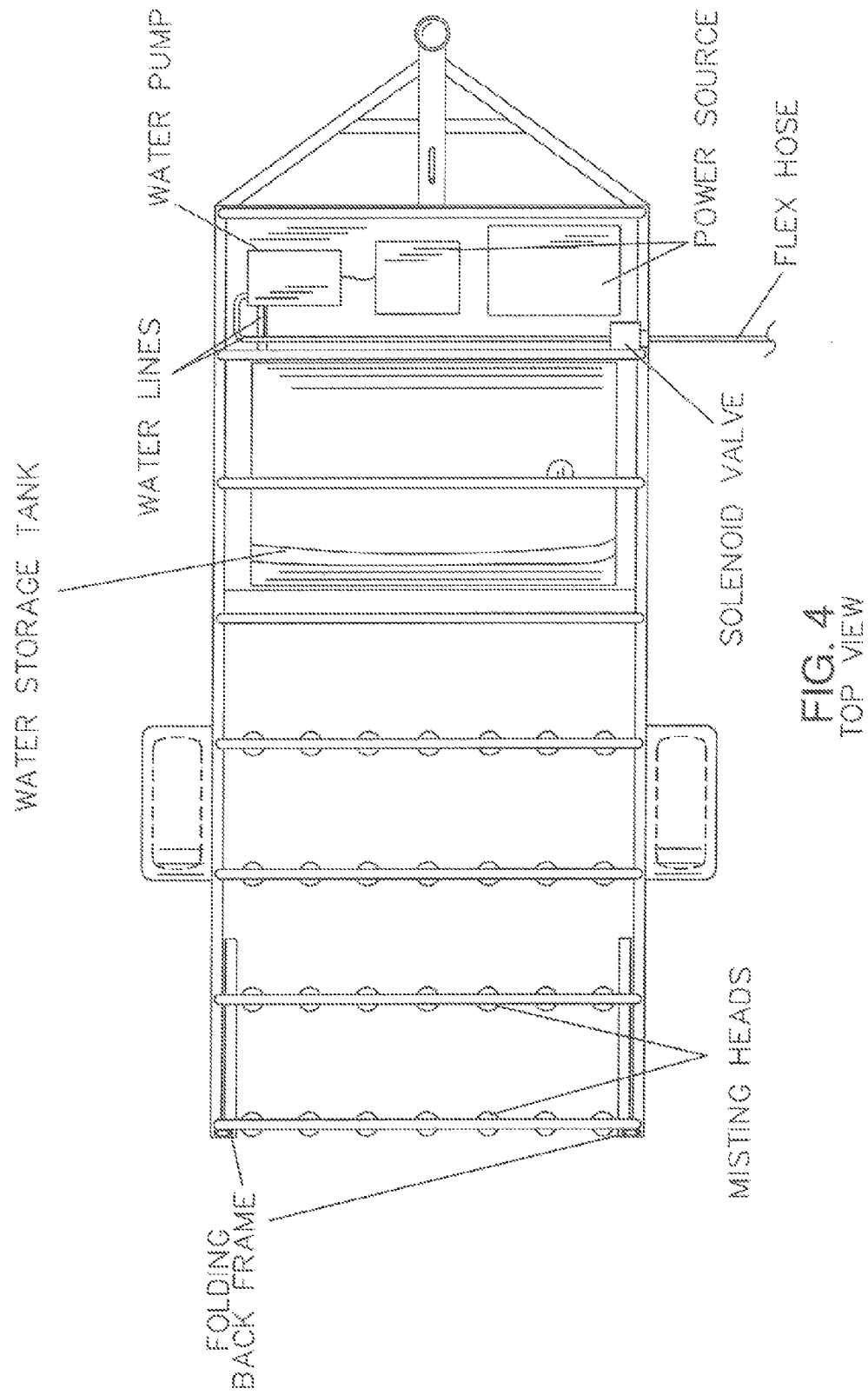
FIG. 4 shows a top view of the portable misting trailer system.
Figure 5:
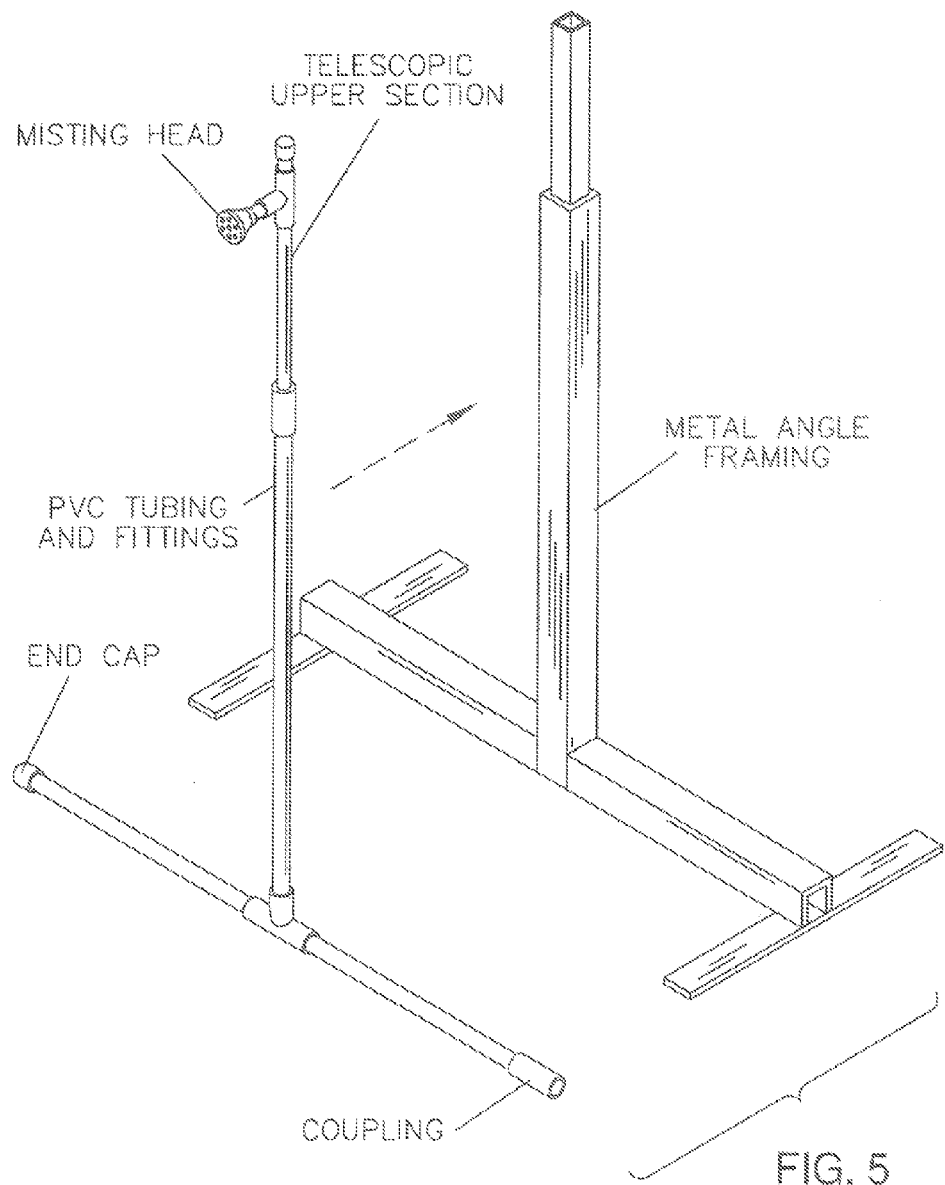
FIG. 5 shows a detail of the auxiliary misting station telescoping arm.
Figure 6:
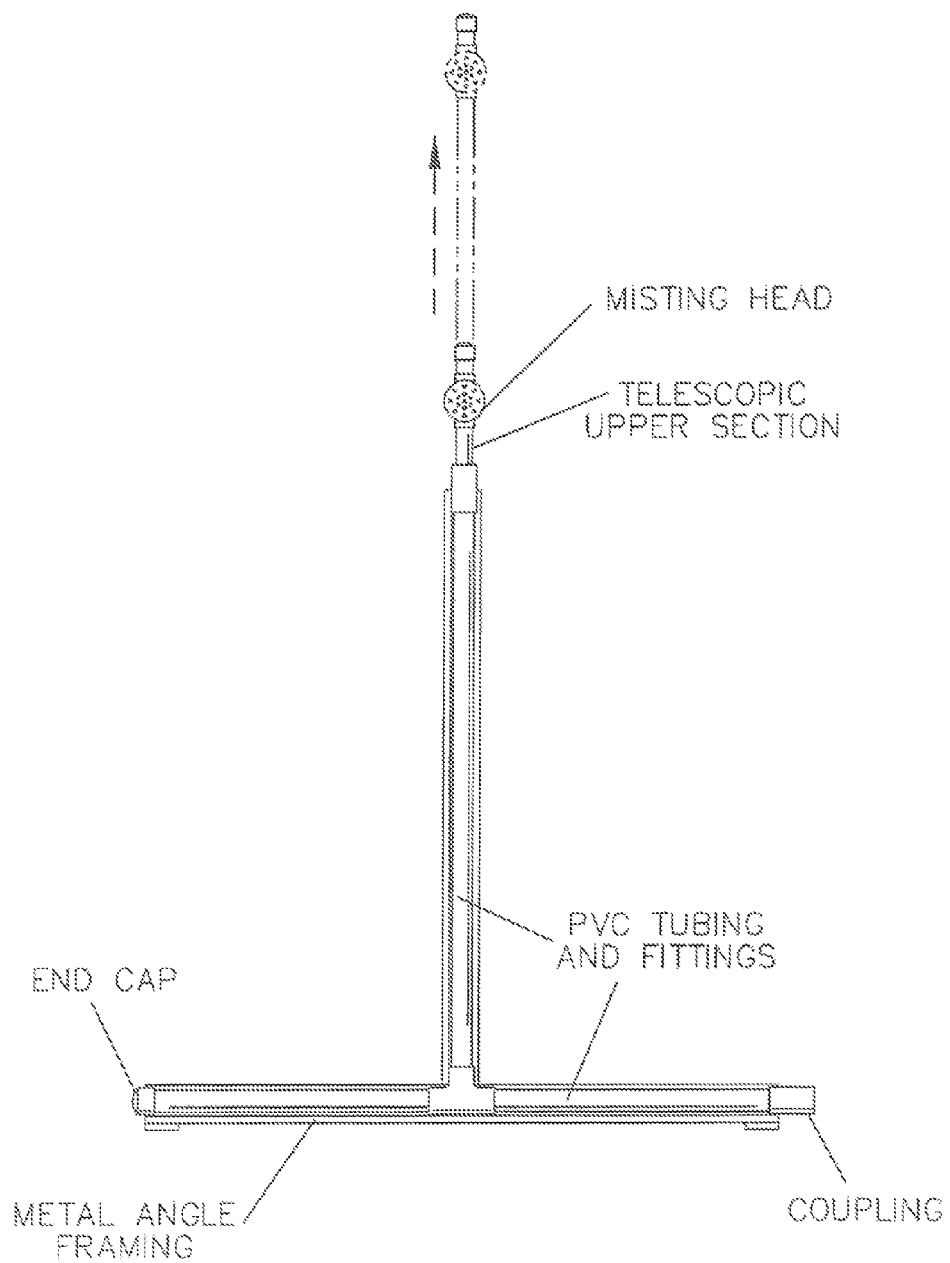
FIG. 6 shows a side view of the auxiliary misting station telescoping arm.
Figure 7:
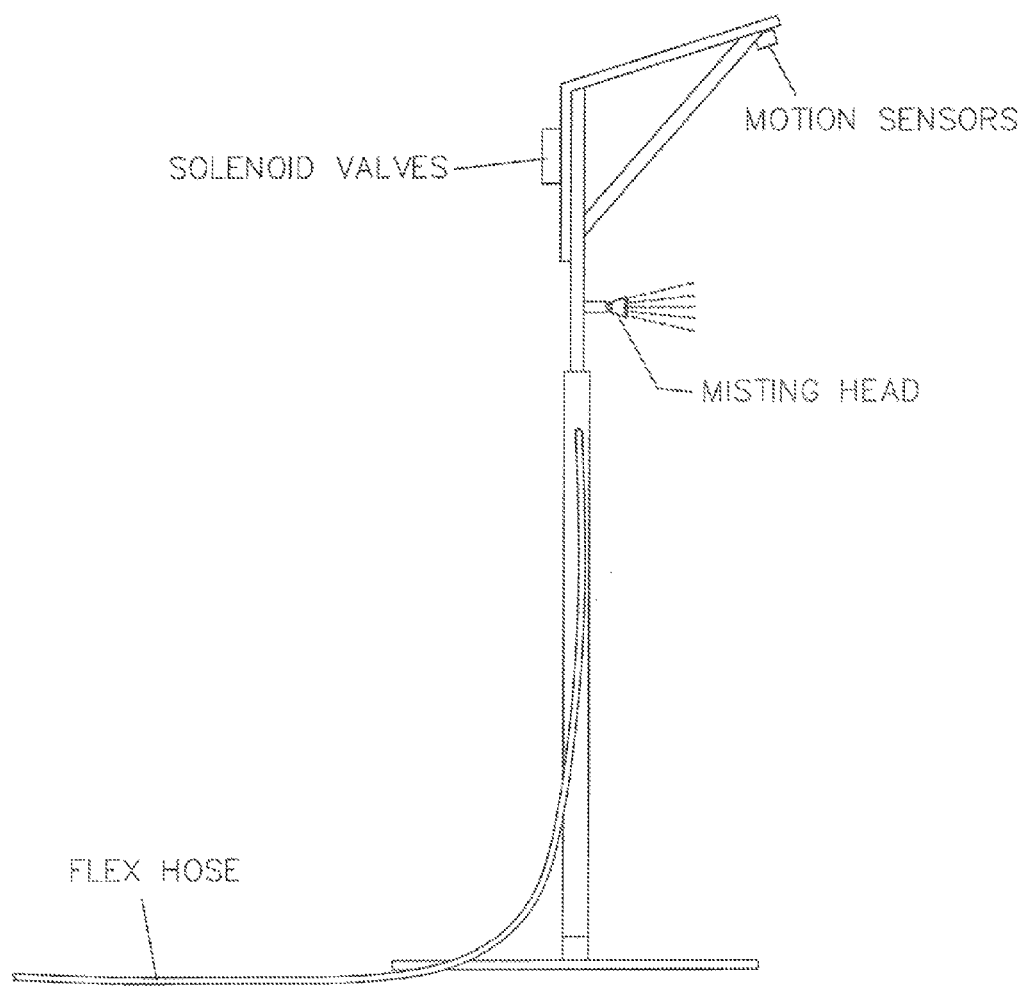
FIG. 7 shows a front view of the auxiliary misting station hose connection.
Figure 8:
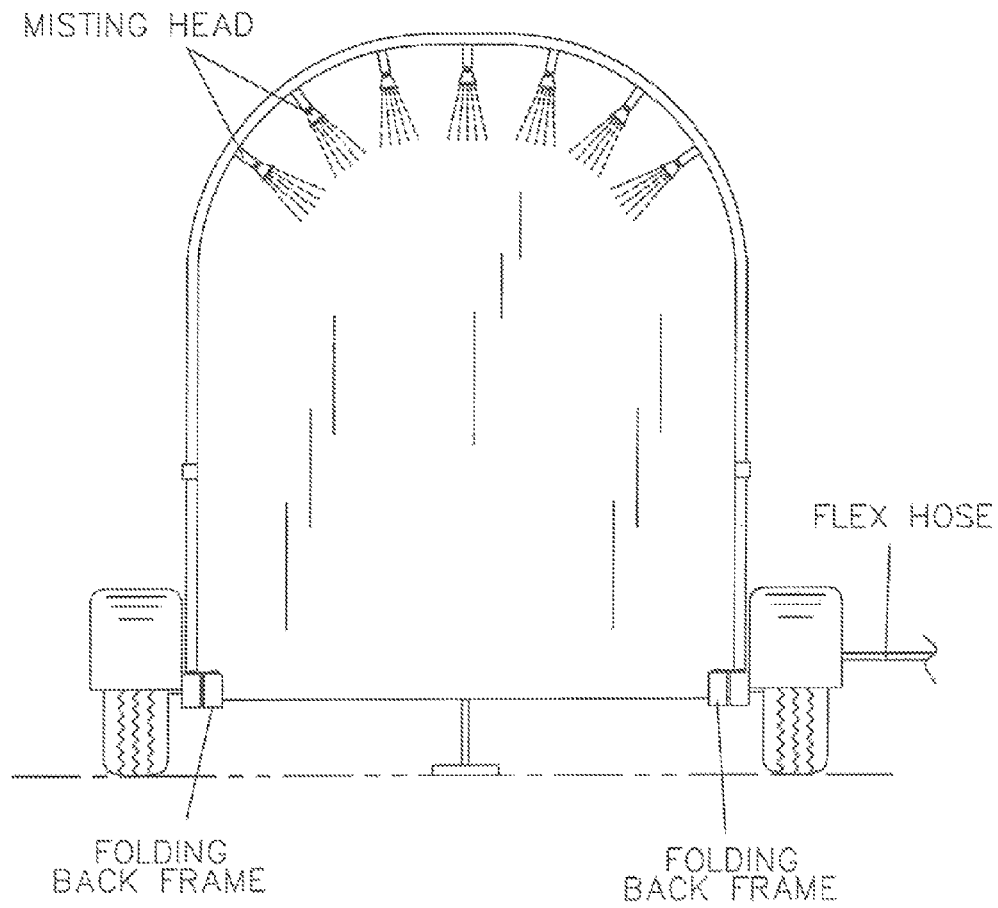
FIG. 8 shows a back view of the portable misting trailer system.
Figure 9:
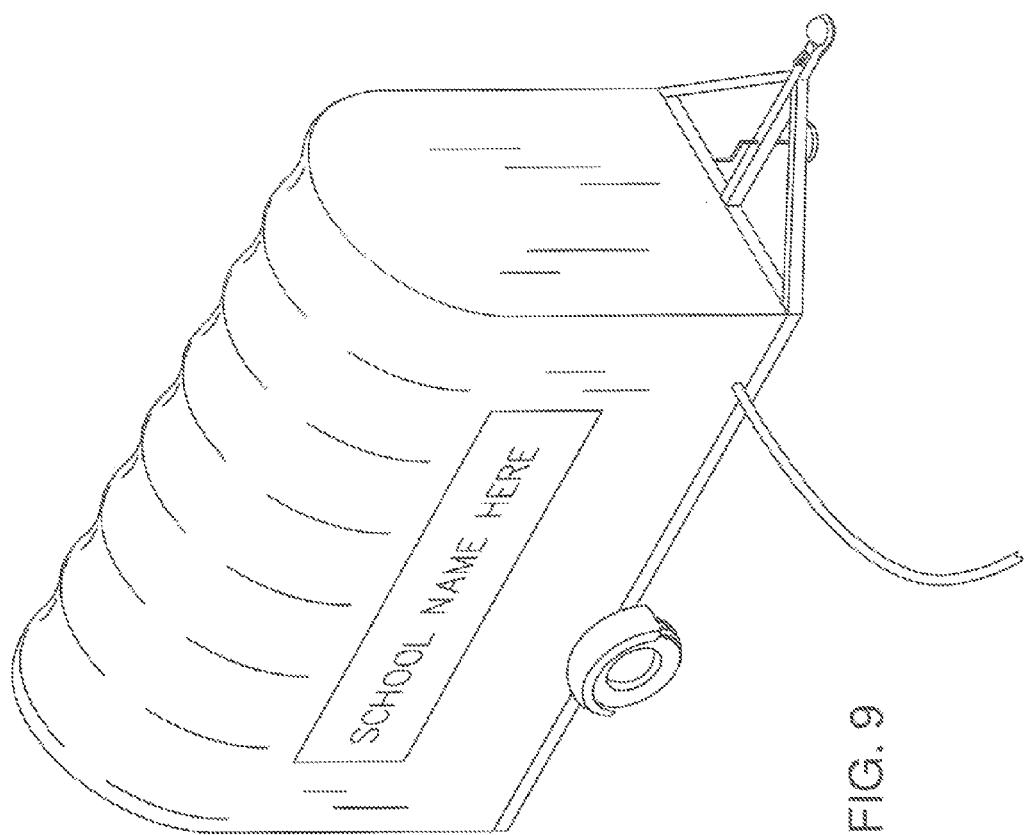
FIG. 9 shows a perspective view of the portable misting trailer system with a cover.

In some embodiments the trailer base (106) is made to open by pivoting the first-folding-back-frame (114) toward the interior front of the trailer and away from the second-folding-back-frame (116), and the second-folding-back-frame likewise pivots toward the interior front of the trailer and away from the first-folding-back-frame (114), so that the first-folding-back-frame (114) comes to rest on the interior of the trailer-base-first-side (113) and the second-folding-back-frame (116) comes to rest on the interior of the trailer-base-second-side (117), thereby regulating access to the misting heads (110). For example, in a reverse manner the first-folding-back-frame (114) and the second-folding-back-frame (116) can be pivoted away from the interior front and sides of the trailer so that the non-pivoting free ends of the folding-back-frames swing to meet and close off access to the misting heads (110). In some embodiments the trailer system further comprises a cover disposed over the arched tubes (108);

Referring now to FIG. 1B, in some embodiments the trailer system further comprises an auxiliary misting station (200), the station comprising: a support base (202) having a first end (201) and a second end (203); a first telescoping arm (204) attaching to and extending upwardly and away from the first end (201) of the support base (202), the first telescoping arm having an upper end and lower end; a second telescoping arm (206) attaching to and extending upwardly and away from the second end (203) of the support base (202), the second arm having an upper end and lower end; a connecting tube (208) which connects the upper end of the first telescoping arm (204) and the upper end of the second telescoping arm (206); a plurality of misting heads (210) disposed on the connecting tube (208) and fluidly connected thereto; a hose (212) fluidly connects the connecting tube (208) with the water system (120), whereupon water would exit the connecting tube (208) via the misting heads (210).

As used herein, the term "about" refers to plus or minus 10% of the referenced number.

The disclosures of the following U.S. Patents are incorporated in their entirety by reference herein: U.S. Pat. No. 5,598,719; U.S. Pat. No. 6,161,362; U.S. Design Pat. No. D488208; U.S. Pat. No. 7,137,269; U.S. Pat. No. 7,334,744; U.S. Pat. No. 7,395,616.

Various modifications of the invention, in addition to those described herein, will be apparent to those skilled in the art from the foregoing description. Such modifications are also intended to fall within the scope of the appended claims. Each reference cited in the present application is, incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A portable misting trailer system (100) for preventing bodies from overheating and regulating body temperature, the system comprising:
    (a) a trailer frame (101) having a first side bar (102) and a second side bar (104), wherein the first and second side bars are secured to a portable trailer base (106);
    (b) a plurality of arched tubes (108) having an arched-tube first end (109) and an arched-tube second end (111), the first end (109) of each tube attaching to the first side bar (102), the second end (111) of each tube attaching to the second side bar (104);
    (c) a plurality of misting heads (110) disposed on the arched tubes and fluidly connected thereto; and
    (d) a water system (120) disposed within the trailer frame (101), the water system comprises a storage tank (122), which is fluidly connected to a water pump (124) that is operatively connected to a power source (126), the power source being operatively connected to an on-off switch;
    wherein the arched tubes (108) are fluidly connected to the water tank (122), whereupon turning on the on-off switch activates the pump (124) to pump water from the water tank (122) into the plurality of the arched tubes (108), whereupon water would exit the arched tubes via the misting heads (110);
    wherein the trailer base (106) further comprises a first wheel (105) rotatably attached to a trailer-base-first-side (113) and a second wheel (107) rotatably attached to a trailer-base-second-side (117); and
    wherein the trailer-base-first-side (113) has a trailer-base-first-side first end (115), and the trailer-base-second-side (117) has a trailer-base-second-side first end (119), and further comprises a first-folding-back-frame (114) pivotably attached to the trailer-base-first-side first end (115) and a second-folding-back-frame (116) pivotably attached to the trailer-base-second-side first end (119).

2. A portable misting trailer system (100) for preventing bodies from overheating and regulating body temperature, the system comprising:
    (a) a trailer frame (101) having a first side bar (102) and a second side bar (104), wherein the first and second side bars are secured to a portable trailer base (106);
    (b) a plurality of arched tubes (108) having an arched-tube first end (109) and an arched-tube second end (111), the first end (109) of each tube attaching to the first side bar (102), the second end (111) of each tube attaching to the second side bar (104);
    (c) a plurality of misting heads (110) disposed on the arched tubes and fluidly connected thereto;
    (d) a water system (120) disposed within the trailer frame (101), the water system comprises a storage tank (122), which is fluidly connected to a water pump (124) that is operatively connected to a power source (126), the power source being operatively connected to an on-off switch; and
    (e) an auxiliary misting station (200), the station comprising:
        (i) a support base (202) having a first end (201) and a second end (203);
        (ii) a first telescoping arm (204) attaching to and extending upwardly and away from the first end (201) of the support base (202), the first telescoping arm having an upper end and lower end;
        (iii) a second telescoping arm (206) attaching to and extending upwardly and away from the second end (203) of the support base (202), the second arm having an upper end and lower end;
        (iv) a connecting tube (208) which connects the upper end of the first telescoping arm (204) and the upper end of the second telescoping arm (206);
        (v) a plurality of misting heads (210) disposed on the connecting tube (208) and fluidly connected thereto;
        (vi) a hose (212) fluidly connects the connecting tube (208) with the water system (120), whereupon water would exit the connecting tube (208) via the misting heads (210).

* * * * *